(12) United States Patent
Jackson et al.

(10) Patent No.: US 10,376,226 B2
(45) Date of Patent: Aug. 13, 2019

(54) METHOD OF IN VIVO MONITORING OF THE CONDITION OF AN INTERNAL SURGICAL REPAIR

(71) Applicant: S. Jackson, Inc., Alexandria, VA (US)

(72) Inventors: Janko Jackson, Alexandria, VA (US); Stephen L. Jackson, Alexandria, VA (US); Crayton G. Toney, Arlington, VA (US)

(73) Assignee: S. Jackson, Inc., Alexandria, VA (US)

( * ) Notice: Subject to any disclaimer, the term of this patent is extended or adjusted under 35 U.S.C. 154(b) by 332 days.

(21) Appl. No.: 15/465,148

(22) Filed: Mar. 21, 2017

(65) Prior Publication Data

US 2017/0188983 A1    Jul. 6, 2017

Related U.S. Application Data

(63) Continuation-in-part of application No. PCT/US2015/053169, filed on Sep. 30, 2015.

(Continued)

(51) Int. Cl.
| | |
|---|---|
| *A61B 6/12* | (2006.01) |
| *A61L 17/10* | (2006.01) |
| *A61L 27/18* | (2006.01) |
| *A61L 27/50* | (2006.01) |

(Continued)

(52) U.S. Cl.
CPC ............... *A61B 6/12* (2013.01); *A61B 5/055* (2013.01); *A61B 5/4851* (2013.01); *A61B 5/7246* (2013.01); *A61B 6/481* (2013.01); *A61B 6/5217* (2013.01); *A61B 8/0833* (2013.01); *A61B 8/481* (2013.01); *A61B 8/5223* (2013.01); *A61B 17/06166* (2013.01); *A61F 2/0063* (2013.01);

(Continued)

(58) Field of Classification Search
CPC ......... A61B 6/12; A61B 5/055; A61B 5/4851; A61B 5/7246; A61B 6/481; A61B 6/5217; A61B 8/0833; A61B 8/481; A61B 8/5223; A61B 17/06166; A61B 2090/3954; A61B 2090/3966; A61B 2090/3925; A61F 2/0063; A61F 2250/0098; A61L 17/04; A61L 27/18; A61L 27/50; A61L 27/56; A61L 17/10
See application file for complete search history.

(56) References Cited

U.S. PATENT DOCUMENTS

| | | | | |
|---|---|---|---|---|
| RE36,370 | E | * 11/1999 | Li | ............................ A61B 17/11 424/443 |
| 6,093,200 | A | 7/2000 | Liu et al. | |

(Continued)

*Primary Examiner* — Sanjay Cattungal
(74) *Attorney, Agent, or Firm* — Stuart J. Friedman

(57) ABSTRACT

A method of in vivo monitoring the condition of an internal body repair in which an imageable, non-absorbable repair device having non-absorbable, particulate imaging material substantially uniformly dispersed therein has been surgically inserted, including: in vivo sensing of dimensional deformation of or imaging material concentration changes in said repair device during the post-surgical healing process; comparing the sensed values with a previously developed correlation between said sensed values and the values at which failure occurs of comparable repair devices; wherein said sensed values relative to the repair device's failure values, considered in conjunction with the anticipated time for complete healing of said repair, provides information as to the condition of the repair.

16 Claims, 1 Drawing Sheet

Related U.S. Application Data

(60) Provisional application No. 62/058,701, filed on Oct. 2, 2014.

(51) Int. Cl.

| | | |
|---|---|---|
| *A61L 27/56* | (2006.01) |
| *A61B 5/055* | (2006.01) |
| *A61B 5/00* | (2006.01) |
| *A61B 6/00* | (2006.01) |
| *A61B 8/08* | (2006.01) |
| *A61B 17/06* | (2006.01) |
| *A61F 2/00* | (2006.01) |
| *A61L 17/04* | (2006.01) |
| *A61B 90/00* | (2016.01) |

(52) U.S. Cl.
CPC ............ *A61L 17/04* (2013.01); *A61L 17/10* (2013.01); *A61L 27/18* (2013.01); *A61L 27/50* (2013.01); *A61L 27/56* (2013.01); *A61B 2090/3925* (2016.02); *A61B 2090/3954* (2016.02); *A61B 2090/3966* (2016.02); *A61F 2250/0098* (2013.01); *A61L 2400/12* (2013.01)

(56) References Cited

U.S. PATENT DOCUMENTS

| | | | |
|---|---|---|---|
| 7,575,734 B2 | 8/2009 | Berkei et al. | |
| 2005/0192581 A1 | 9/2005 | Molz et al. | |
| 2006/0129216 A1* | 6/2006 | Hastings | A61B 5/0215 607/115 |
| 2006/0182907 A1 | 8/2006 | Atanasoska et al. | |
| 2009/0076594 A1 | 3/2009 | Sabaria | |
| 2009/0130186 A1* | 5/2009 | McCarthy | A61F 13/00995 424/445 |
| 2011/0165221 A1* | 7/2011 | Jung | A61F 13/00008 424/445 |
| 2015/0283287 A1* | 10/2015 | Agarwal | A61F 13/02 424/444 |
| 2015/0327861 A1* | 11/2015 | Jackson | D06M 15/59 606/224 |
| 2017/0232157 A1* | 8/2017 | Rege | A61L 31/128 606/214 |
| 2017/0360554 A1* | 12/2017 | Linderman | A61B 17/06166 |
| 2018/0228938 A1* | 8/2018 | McGuire | A61L 27/50 |
| 2018/0289857 A1* | 10/2018 | Rafat | A61L 27/24 |

\* cited by examiner

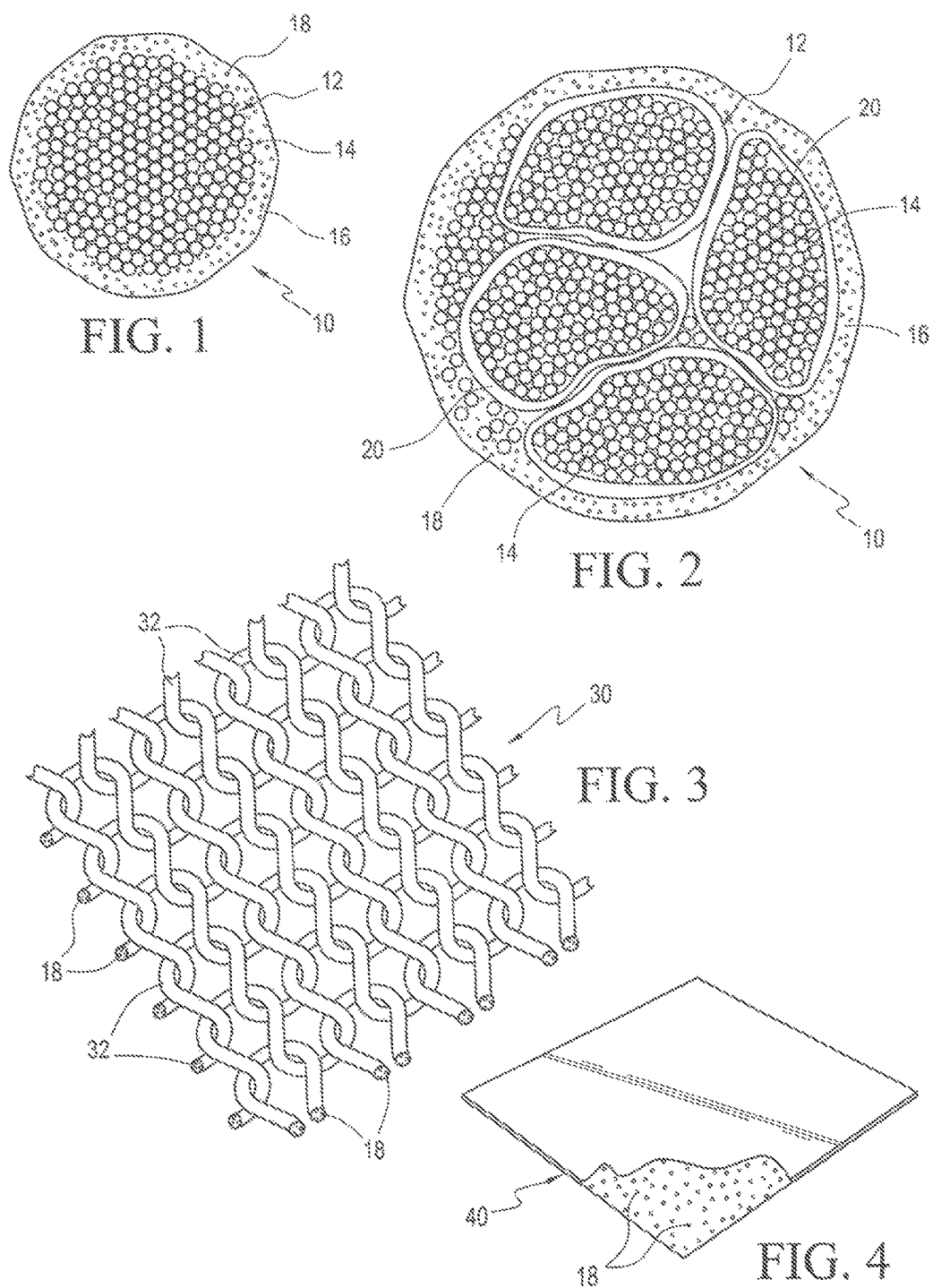

METHOD OF IN VIVO MONITORING OF THE CONDITION OF AN INTERNAL SURGICAL REPAIR

FIELD OF THE INVENTION

The present invention relates to elastic, stretchable, polymeric, non-absorbable surgical repair devices having an imaging material dispersed therein and, more particularly, to a method of in vivo monitoring the condition of an internal surgical repair in a living thing in which such repair devices have been surgically inserted within the body to effect the repair.

BACKGROUND OF THE INVENTION

Following many surgical procedures in a living thing (human or animal) it is important or advantageous to be able to monitor in vivo the condition of surgical repair devices inserted during the procedure in order to monitor the healing progress of the surgical repair. Surgical repairs may fail, require repair or require removal for any number of reasons, including, inter alia, foreign body rejection, poor surgical repair device insertion, surgical repair device stretching or deforming and breaking or failure in some other detrimental fashion.

Typically useful surgical repair devices include non-absorbable polymeric sutures, which may be monofilamentary or multifilamentary and formed of polyamides or other synthetic polymers. Also in common use are polymeric foil and mesh implants. Foil implants are smooth polyamide or other synthetic polymeric, substantially planar sheets having a thickness from 0.01-2.0 mm. Mesh implants are woven or knit material of open texture formed of polyamide or other synthetic polymeric fabric.

Heretofore, surgical devices, such as stents, have been inserted into body lumens to maintain open lumen passageways and external imaging devices have been used to assure the accuracy of stent insertion and to monitor stent placement in the lumens. This monitoring, however, does not address the condition of the affected body part and does not inform the physician regarding the healing status of the body part. Illustrative of this is U.S. Patent Application Publication 2009/0076594, dated Mar. 19, 2009 to Sabaria which discloses stents which are generally cylindrical in configuration and formed of biodegradable, biocompatible and bioresorbable materials. The stents include one or more discrete or coated markers which may be detected external to the body by conventional imaging means, such as x-ray or other electromagnetic radiation detection methods, MRI or ultrasound, Preferably, the markers are applied by crimping a ribbon onto a strut of the stent, by partially sputtering a heavy metal coating onto all or part of the stent, or by any number of other techniques. The markers are used to monitor the deployment and placement of the stent at desired locations within lumens. Certain types of markers may be used to monitor the length, diameter and 3-D orientation of the stent in the lumen. However, for these purposes only discrete markers can be used which are specifically and accurately located on the stent in order to allow examining the location of the markers relative to one another. Thus, to determine stent length, first and second discrete markers are crimped onto the stent such that their spatial orientation is such that they lie on a line with a component vector parallel to the longitudinal axis of the stent. To determine stent diameter, first and second discrete markers are crimped onto the stent such that their spatial orientation is such that they lie on a line with a component vector perpendicular to the longitudinal axis of the stent. Likewise, to determine 3-D orientation, first and second discrete markers are crimped onto the stent such that their spatial orientation is such that they lie on a line with a component vector perpendicular to the longitudinal axis of the stent plus a third discrete marker is crimped onto the stent such that its spatial orientation is such that it lies on a line with a component vector parallel to the longitudinal axis of the stent. From this requirement for discrete markers to be placed at specific locations with specific orientations it follows that in order to have the ability to make dimensional measurements of the stent, the markers may not be uniformly dispersed throughout the stent. It is also noteworthy that these dimensional stent measurements bear no relevance whatever to the condition of the affected body part and do not inform the physician regarding the healing status of the body part. Likewise the use of these discrete markers to monitor the rate of pre-programmed degradation of different regions of the stent also bears no relevance whatever to the condition of the affected body part and does not inform the physician regarding the healing status of the body part.

It is, therefore, apparent that prior methods for monitoring surgical repair devices inserted within a living body were never intended to and do not provide a method of in vivo monitoring the condition of an internal surgical repair in a living body in which such repair devices were surgically inserted to effect the repair.

SUMMARY OF THE INVENTION

In accordance with one aspect, the present invention provides a method of in vivo monitoring the condition of an internal body repair in a human or animal in which an imageable, non-absorbable repair device, having non-absorbable, particulate imaging material substantially uniformly dispersed therewithin, which device deforms due to stresses of the healing process, has been surgically inserted within the body to effect the repair, comprising:

in vivo sensing using an external to the body imaging device by a medical practitioner of dimensional deformation of or imaging material concentration changes in said imageable repair device during the post-surgical healing process;

comparing the sensed imaging material concentration changes or dimensional deformation with a previously developed correlation between said sensed imaging material concentration or dimensional deformation and the value of said imaging material concentration or dimension at which failure occurs of repair devices having comparable size, construction and chemical composition characteristics;

wherein said sensed value of said imaging material concentration or dimension relative to the repair device's failure value of said imaging material concentration or dimension, considered in conjunction with the anticipated time for complete healing of said repair, provides information to said medical practitioner as to the condition of the repair and is indicative of whether medical or surgical intervention is appropriate.

In another aspect of the invention, there is provided a method wherein said in vivo sensing and comparative analysis occurs repetitively at spaced time intervals subsequent to repair device insertion.

In still another aspect of the invention, there is provided a method wherein said dimensional deformation of said imageable repair device is a decrease in the diameter of said repair device over a predetermined length of device.

In yet another aspect of the invention, there is provided a method wherein said change in imaging material concentration in said imageable repair device is a change in the concentration of imaging material over a predetermined length of device.

In another aspect of the invention, there is provided a method wherein said previously developed correlation is an in vivo correlation.

In yet another aspect of the invention, the imaging material is particulate nanoparticles detectable by x-ray, electromagnetic radiation, MRI or ultrasound imaging devices.

In yet another aspect of the invention, there is provided a method wherein said imageable repair device is a radiopaque repair device having non-absorbable, particulate radiopaque material substantially uniformly dispersed therewithin.

In still another aspect of the invention, the radiopaque repair device comprises non-absorbable, polymeric sutures.

In yet another aspect of the invention, there is provided a method wherein the healing process of an internal surgical repair in a human or animal body may be monitored by utilizing the unique properties of surgically inserted non-absorbable, polymeric repair devices having non-absorbable, particulate imaging material substantially uniformly dispersed therewithin using imaging devices such as x-rays, MRI and ultrasound which are external to the body and which are capable of visualizing physical shape, distortion of physical shape, shifting of longitudinal or radial layers of the repair devices as well as detection and quantification of the physical location and concentration of the imaging materials within the repair device.

BRIEF DESCRIPTION OF THE DRAWINGS

FIG. 1 is a cross-sectional view of an extrusion coated multifilament, non-absorbable radiopaque suture wherein the suture core comprises a multitude of polyamide filaments twisted or braided together and heat set and the overlying sheath contains substantially uniformly dispersed imaging material, such as radiopaque material.

FIG. 2 is a cross-sectional view of an extrusion coated multifilament, non-absorbable radiopaque suture wherein the suture core comprises a mixture of polyamide filaments and previously extruded bundles comprising a multitude of individual polyamide filaments twisted or braided together, heat set and overcoated with a polyamide sheath containing substantially uniformly dispersed imaging material, such as radiopaque material.

FIG. 3 is a perspective view of a surgical mesh incorporating substantially uniformly dispersed imaging material, such as radiopaque material, in the synthetic polymeric fabric.

FIG. 4 is a perspective view of a smooth synthetic polymeric foil implant incorporating substantially uniformly dispersed imaging material, such as radiopaque material, in the synthetic polymeric sheet.

DETAILED DESCRIPTION OF THE INVENTION

The present invention provides a method of in vivo monitoring the condition of an internal surgical repair in the body of a living thing in which imageable, non-absorbable, polymeric repair devices have been surgically inserted within the body to effect the repair. Repair devices which are typically useful include, but are not limited to, non-absorbable surgical sutures, polymeric foil and polymeric mesh implants. The non-absorbable, polymeric repair devices must, in order to achieve the desired monitoring, be visualizable in vivo utilizing imaging and sensing equipment to detect and quantify the distortion of the geometric dimensional deformation and imaging material concentration changes in the in vivo repair device during the post surgical healing of the surgical repair, as well as the shifting of longitudinal or radial layers of the repair device. To accomplish this each repair device includes imaging particles, desirably nanoparticles, substantially uniformly dispersed within the repair device to allow external sensing of the dimensional and imaging material concentration changes within the repair device, as well as mapping of the imaging particle migration within the repair device, during the post surgical healing process. This sensing and quantification of changes to the repair device allows comparing the condition of the repair device at any moment in time with a previously developed correlation between such repair device characteristics and their value at which failure of the repair device occurs. This comparison informs the physician of the condition of the repair device and of the healing status of the body part.

Visualization of the uniquely informative property changes of the imaging particles during surgical repair healing may be sensed and detected by x-ray or other electromagnetic radiation detection methods, magnetic resonance imaging (MRI) and sonography, the latter being a type of medical diagnostic imaging that uses high frequency sound waves, also known as ultrasound, to produce images of organs, tissues, blood flow and non-absorbable surgical repair devices having imaging particles dispersed therein. When utilizing x-ray or other electromagnetic radiation detectors, the preferred imaging particles are radiopaque particles which are opaque to one or another form of electromagnetic radiation. As used herein, the prefix "radio" is intended to include all radiation in the radio frequency domain which is useful for medical imaging purposes. MRI visibility is achieved by use of a particle that generates a magnetic susceptibiltity artifact such as a paramagnetic, ferromagnetic, non-ferromagnetic, or superparamagnetic substance. Sonographic visibility is achieved using imaging particles detectable by high frequency sound waves, which includes substantially all of the particle types suitable for electromagnetic radiation and MRI detection.

The method of the present invention is widely applicable to many types of surgical repairs. It is, nevertheless, particularly useful for monitoring the healing progress following tendon or cruciate repair using sutures or hernia repairs using mesh or orbital floor repairs using smooth foil implants. To illustrate and highlight the importance of monitoring the healing process post surgical repair it is important to consider an example of a surgical repair which benefits greatly from post surgical monitoring, such as end to end tendon repairs. In this particular procedure it is widely accepted that it is most desirable to have and maintain during the healing process the smallest possible gap between the tendon ends. This is important because that gap must be filled with granulation tissue during the entire healing process for successful healing to take place.

In typical tendon repair the ideal gap between tendon ends is less than one millimeter. However, in practice this may not always be possible depending on many factors, including which of the various techniques for end to end tendon repair may have been used. In any event, the smaller the gap between the tendon ends, the more quickly the gap will be filled by collagen and thus mature. This end to end tendon juncture is the weakest link in tendon repair and will be the first to yield under tension. The juncture will stretch before catastrophic rupture. The amount of stretch during healing is directly proportional to the load on the tendon and the unit length of the collagen material filling the gap. As the juncture stretches, the collagen material mass remains constant but changes shape, narrowing at the point of greatest stress and increasing the size of the juncture gap. This weakens the repair and can lead to catastrophic failure of the end to end tendon repair.

The actual technique used for end to end tendon repair and the suture material used are of critical importance to this healing process. Many studies have been performed to determine the "best" including investigations of the Bunnell criss-cross technique, traditional repair with four simple sutures, the baseball stitch, the long mattress stitch, the short mattress stitch, and the lateral trap suture.

Typically in such studies, the comparisons of the different techniques and suture materials are made through measurements of (1) the destructing force which produces the gap between the tendon ends and (2) the force causing the ultimate rupture of the suture and the catastrophic failure of the repair. While such studies offer valuable guidance regarding alternative techniques and suture materials, they serve no purpose for in vivo diagnosis during the post surgical healing process.

To this end, and in light of the issues affecting good end to end tendon repair results the present invention provides novel methods for in vivo monitoring of the healing process. These novel methods can be used to characterize, measure, and quantify the status of the surgical suture material used in the repair and thereby assess the strength of the juncture gap. This in turn, allows diagnosis of the end to end tendon repair healing process in vivo.

Inasmuch as all but metal surgical repair devices are transparent to visualization, and the use of metal repair devices is frequently undesirable, it has been found that only the use of non-absorbable, polymeric repair devices having imaging properties provides the capability of monitoring the healing progress of a surgical repair. Polymeric surgical repair devices require a unique combination of physical properties. They must be nonirritating, flexible and exhibit high tensile strength. Additionally, they must retain their physical properties after conventional processing such as sterilization and resterilization. The most frequently used surgical repair devices are non-absorbable polymeric sutures, although other well known non-absorbable polymeric repair devices, including but not limited to polymeric mesh and foil implants, are useful in the monitoring method of the present invention.

For ease of description and understanding, the instant method will be described herein primarily using non-absorbable, polymeric sutures which incorporate substantially uniformly dispersed radiopaque particles as the imaging material as the surgical repair devices, although the method described is readily adaptable to use with devices other than sutures. One recently developed suitable polymeric radiopaque suture is described in pending U.S. Patent Application Publication No. 2015/0327861, published Nov. 19, 2015, and assigned to the same assignee as the present invention, the disclosure of which is incorporated herein by reference.

Polymeric sutures must, in addition to the aforementioned physical properties, exhibit high knot strength. Additionally, sutures must retain their physical properties after conventional processing such as dyeing, sterilization and resterilization. Some elasticity is required in the final suture structure to obtain the required knot strength and other properties to allow the suture to meet USP specifications. Sutures may be visualized in real time using imaging devices external to the body and may be made radiopaque by incorporating nanoparticle sized imaging material substantially uniformly dispersed throughout the entire length of the suture. In one useful suture construction, as described in the aforementioned U.S. patent application publication, the suture comprises a core of a plurality of twisted Polyamide 66 filaments encased within a sheath of Polyamide 6 in which nanoparticle radiopaque materials, such as tantalum or other radiopaque particles, are substantially uniformly dispersed to provide the desired radiopacity along the entire length of the suture.

Referring to FIG. 1, there is shown a cross section of an illustrative radiopaque suture 10 useful in connection with the method of the present invention. Suture 10 comprises a core 12 formed of a multitude of Polyamide 66 fibers 14 and an overcoated Polyamide 6 sheath 16 having nanoparticle sized radiopaque material 18 substantially uniformly dispersed throughout the thickness and length of sheath 16. Another form of suture useful in the method of the present invention is shown in FIG. 2, which illustrates a core 12 formed of previously extruded bundles 20 of Polyamide 66 filaments 14 overcoated with a Polyamide 6 sheath 16, the core 12 being encased within sheath 16 which has been extruded thereabout, the sheath 16 having nanoparticle sized radiopaque material 18 substantially uniformly dispersed throughout its thickness and length. Optionally, core 12 may include, in addition to bundles 20, individual Polyamide 66 filaments 14 to act as a filler in some of the spaces formed between the bundles 20. The sheath-core configuration of the multifilament sutures requires that the polyamide core filaments have at least a 30° C. greater melting temperature than the polyamide sheath material to assure that the filaments in the core do not melt during over coating of the sheath. Non-absorbable suture constructions such as shown in FIGS. 1 and 2, without the incorporation of radiopaque material 18 substantially uniformly dispersed throughout sheath 16, are well known and marketed under the trademark SUPRAMID® and SUPRAMID EXTRA® in the U.S. by S. Jackson, Inc. of Alexandria, Va.

Referring to FIG. 3, there is shown an illustrative polymeric mesh 30 which is a woven or knit material of open texture formed of polyamide, e.g., Polyamide 6, or other synthetic polymeric fabric. The threads 32 forming the mesh correspond to the radiopaque sutures of FIG. 1 or 2 and, therefore, include nanoparticle sized radiopaque material 18 substantially uniformly dispersed throughout the thickness and length of each thread. Another form of surgical device is shown in FIG. 4, which illustrates a foil implant 40 comprising a smooth polyamide, e.g., Polyamide 6, or other synthetic polymeric sheet having a thickness from 0.01-2.0 mm and having incorporated within the sheet during its formation nanoparticle sized radiopaque material 18 substantially uniformly dispersed throughout the thickness of the sheet.

It will be appreciated that these forms of radiopaque surgical repair devices are only illustrative of the type of radiopaque surgical repair devices which are useful in the method of the present invention. Other device constructions and other polymeric materials may be used to form imageable sutures, meshes, foils, and the like, useful in the method of the present invention, provided that the imaging material is substantially uniformly dispersed to provide the desired visualization throughout the entire device. When radiopaque materials are used as the imaging material, the preferred radiopaque material is nanoparticulate tantalum or tantalum oxide, which are known to be highly bioinert and to possess high radiographic density, allowing them to be used at relatively lower concentrations. However, due to the high cost of tantalum compounds, its use may not always be economically practical. Other highly desirable radiopaque materials include, for example, titanium, zirconium, silver, bismuth and platinum in elemental, salt or oxide form. Consistent with the foregoing criteria, still other radiopaque materials may be used as well. However, inasmuch as the concentration of radiopaque particles in the device is a function of the radiopacity of the particle selected, some radiopaque materials are unsuitable due to the high concentrations which would be required to achieve the desired radiopacity.

It is well known that elastic, polymeric sutures stretch and that when they are placed under tension they elongate and can ultimately fail. For example, available data suggests that failure of polyamide sutures occurs generally somewhere between 20% and 30% elongation, depending upon the characteristics of the particular suture. As the suture elongates under stress, the suture diameter decreases thus decreasing the amount of particulate radiopaque material within a fixed length of the suture. It has been found that this decrease in the density or concentration of radiopaque material within the fixed length of the suture as a function of elongation can be measured in vivo for any particular suture. It has also been found that the decrease in suture diameter within a fixed length of the suture as a function of elongation can be measured in vivo for any particular suture. Accordingly, the present invention provides a number of methods for monitoring the progress of healing of a sutured repair within the body of a mammal by quantitative in vivo monitoring the condition of an elastic, stretchable polymeric suture having a radiopaque material substantially uniformly dispersed therein along its length which has been inserted into the body in a surgical procedure. The ultimate goal of the methods is to provide totally reliable in vivo measurement of the healing process following surgical repairs by taking advantage of the change in physical and/or imaging material concentration characteristics during healing of surgically inserted radiopaque polymeric, non-absorbable repair devices.

Initially, the in vivo relationship between radiopaque material concentration in a fixed length of the suture and corresponding suture elongation is empirically determined, e.g., via cadaver studies, for the particular radiopaque suture to be used. This includes determining the radiopaque material concentration at which suture rupture occurs due to elongation. With this relationship available, it would be prudent for the physician, substantially immediately following surgical repair using radiopaque sutures, to order a study of the sutured repair to measure in vivo the radiopaque material concentration in a fixed length of the suture within the body. This determines the base line concentration of radiopaque material in said suture before any elongation occurs. As used herein, the term "substantially immediately" is intended to refer to a time frame following the surgical procedure which is sufficiently short to avoid suture elongation. This base line concentration of radiopaque material in the suture is converted, using the developed relationship of radiopaque material concentration to corresponding suture elongation, into terms of suture elongation. The physician is primarily concerned with the status of the repair sutures during the period between insertion and full healing. During that period if elongation of the suture occurs, then the diameter of the suture and/or the thickness of the radiopaque material containing portion of the suture will diminish and the density or amount or concentration of radiopaque material within the fixed length of suture will also diminish. The extent of any elongation of the sutures will be evident by comparing the suture elongation corresponding to each periodically determined radiopaque material concentration measurement to the base line suture elongation, to any previously measured suture elongations and to the suture rupture elongation to determine the condition of the suture relative to its base line and to its rupture elongation at any time during the healing process. This information will allow a physician to determine whether the sutured repair is healing properly or is damaged and, if the latter, the seriousness of the damage and whether medical or surgical intervention is appropriate. Alternatively, particularly where healing occurs over a shorter term, the physician may elect to make only one in vivo measurement of the radiopaque material concentration in a fixed length of the sutures at a selected time following surgical insertion and, using the developed relationship of radiopaque material concentration to suture elongation and suture failure, determine whether suture elongation has occurred and, if so, how close the sutures are to suture rupture elongation.

In another illustrative embodiment the suture material is subjected to stress tests in an environment similar to that which exists when in use. Wherever possible, the stress tests should be conducted under simulated in vivo conditions to account for any chemical embrittlement or dissolution effects. The stress-strain relationship of the suture from onset of elongation all the way to failure, including evaluation of the deformation by optical microscopy and scanning electron microscopy (SEM), can be accomplished. Pulling or stretching stress is applied to a suture specimen within an SEM, which allows a measurement of the suture diameter over a fixed length of suture and a calculation of the decrease in suture diameter over a fixed length of the suture at increasing increments of applied stress up until suture failure. This provides, for each suture tested, a relationship between the measured decrease in suture diameter at each increment of applied stress, including the unstressed or base line suture diameter (at zero percent decrease in suture diameter) and the failure diameter. With this relationship available, it would be prudent for the physician, substantially immediately following surgical repair using radiopaque sutures, to order a study of the sutured repair to measure in vivo the radiopaque material concentration in a fixed length of the suture within the body. This determines the base line concentration of radiopaque material in said suture before any elongation occurs. As used herein, the term "substantially immediately" is intended to refer to a time frame following the surgical procedure which is sufficiently short to avoid suture elongation. This base line concentration of radiopaque material in the suture is converted, using the previously developed relationship of radiopaque material concentration to corresponding suture elongation, into terms of suture elongation or diameter. Alternatively, the physician could order at this time an in vivo visualization of the suture diameter over a fixed length of suture to obtain a base line suture diameter. Again, the physician is primarily concerned with the status of the repair sutures during the period between insertion and full healing. During that period in vivo visualizations of the suture diameter over a fixed length of suture are periodically made, for example, by X-ray, MRI, CAT scans, ultrasound, or other visualization technique which may be most appropriate and compared to the previously developed relationship of suture diameter to stress for the particular suture in use. If stretching of the suture occurs, then the diameter of the suture over the fixed length will diminish and the extent of any diameter decrease will be evident by comparing the diameter decrease corresponding to each periodically determined visualization to the base line suture diameter, to any previously measured suture diameter and to the suture rupture diameter to determine the condition of the suture relative to its base line and to its rupture condition at any time during the healing process. This information will allow a physician to determine whether the sutured repair is healing properly or is damaged and, if the latter, the seriousness of the damage and whether medical or surgical intervention is appropriate. Alternatively, particularly where healing occurs over a shorter term, the physician may elect to make only one in vivo visualization of the suture diameter over a fixed length of the sutures at a selected time following surgical insertion and, using the previously developed relationship of suture diameter reduction to suture elongation and suture failure, determine whether suture elongation has occurred and, if so, how close the sutures are to suture rupture elongation.

Particularly for multifilament sutures which include a core and a sheath, as previously described, it may be informative to know whether the sheath is failing prior to the core and, if so, how much prior. This information can be determined, if it occurs, during the aforementioned stress tests using optical microscopy and SEM. If sheath failure prior to suture failure is noted, it is noteworthy at what radiopaque suture concentration or suture diameter reduction the sheath failure occurs. This will furnish the physician with still another data point to assist in determining the condition of the sutured repair relative to the anticipated time for complete healing of the repair. For example if, hypothetically, for a particular type and size of suture, it is known that sheath failure occurs very shortly prior to suture failure, then the physician will know that if sheath failure has occurred, then some medical or surgical intervention is likely warranted. Conversely, if, hypothetically, for a particular type and size of suture, it is known that sheath failure occurs well prior to suture failure, then sheath failure can be used as an indication of approximately how long it may be before complete suture failure and, depending upon the time to complete healing, whether any medical or surgical intervention is warranted.

In a particularly desirable embodiment of the invention, the task of comparing imaging material concentration measurements, suture diameter measurements, suture elongation measurements and the like and signaling to the physician, where appropriate, that the surgical repair is damaged to the extent that medical or surgical intervention may be warranted is achieved by linking the output of visualization equipment (e.g., x-ray, MRI, ultrasound) to a computer which has previously been furnished relevant information regarding the behavior of the particular surgical repair device under healing stress as well as prior periodic post surgical in vivo measurements of the repair device. Thus, for example, if the surgical repair device is non-absorbable sutures containing imageable material uniformly dispersed therein, and the relevant measurement is diameter of the suture over a fixed length of suture, the computer would have stored in its memory information relevant to the particular suture type comprising, at least, the known changes of suture diameter over a fixed length of suture with applied stretching stress, the base line in vivo post surgical suture diameter over a fixed length of suture before healing occurs, prior periodic post surgical in vivo measurements of the suture diameter over a fixed length of suture and the suture diameter over a fixed length of suture at which suture rupture occurs. In addition, the computer would have in its memory the anticipated normal healing time for the particular surgical repair. Armed with this information and programmed with an appropriate algorithm for comparing and evaluating the measurements fed to it by the visualization equipment, the computer is able to assess the healing progress of the surgical repair. If desired, the computer could be made to provide an alert signal to the physician, for example, in the form of a visual or audible signal to any external system, to alert the physician to the existence of a wound healing condition potentially requiring attention or intervention.

It should be appreciated that the goal of providing quantitative in vivo monitoring of the healing process following surgical repair by using the unique properties of radiopaque sutures is merely illustrated by the methods disclosed herein and is equally applicable to other imaging material surgical repair devices. The ability to quantify the healing process is of great diagnostic importance in procedures like tendon repair, hernia repair and wherever monitoring of a long-duration healing process is necessary. It will provide timely alert of potential catastrophic failure of the surgical repair. To this end it will be seen that the goal is achieved by, where appropriate, characterizing the suture failure mechanism, determining the optimum or, at least, functional indicia of suture failure and the sensor or instrumentation best able to accurately provide the necessary data for assessing the various stages of suture degradation prior to failure. This information is vital to developing monitoring guidelines, in the nature of charts, tables, algorithms, and the like, including reliable sensing instrumentation, for the physician to use in assessing whether the sutured repair is healing properly or is damaged and, if the latter, the seriousness of the damage.

While the present invention has been described in terms of specific embodiments thereof, it will be understood that no limitations are intended to the details of construction or design other than as defined in the appended claims.

The invention claimed is:

1. A method of in vivo monitoring the condition of an internal body repair in a human or animal in which an imageable, non-absorbable repair device, having non-absorbable, particulate imaging material substantially uniformly dispersed therewithin, which device deforms due to stresses of the healing process, has been surgically inserted within the body to effect the repair, comprising:
   a) in vivo sensing using an external to the body imaging device by a medical practitioner of imaging material concentration changes in said imageable repair device during the post-surgical healing process;
   b) comparing the sensed imaging material concentration change with a previously developed correlation between said sensed imaging material concentration and the value of said imaging material concentration at which failure occurs of repair devices having comparable size, construction and chemical composition characteristics;
   c) wherein said sensed value of said imaging material concentration relative to the repair device's failure value of said imaging material concentration, considered in conjunction with the anticipated time for complete healing of said repair, provides information to said medical practitioner as to the condition of the repair and is indicative of whether medical or surgical intervention is appropriate.

2. A method, as claimed in claim 1, wherein said in vivo sensing and comparative analysis occurs repetitively at spaced time intervals subsequent to repair device insertion.

3. A method, as claimed in claim 1, wherein said change in imaging material concentration of said repair device is a decrease in the concentration of imaging material over a predetermined length of device.

4. A method, as claimed in claim 1, wherein said previously developed correlation is an in vivo correlation.

5. A method, as claimed in claim 1, wherein said repair device is formed of a polyamide.

6. A method, as claimed in claim 1, wherein said repair device comprises a filamentary core and a sheath surrounding said core along its length, said sheath having substantially uniformly dispersed therein non-absorbable radiopaque nanoparticles, and said sensed imaging material concentration change is a decrease in the concentration of one or more detected elements within a predetermined length of said repair device.

7. A method, as claimed in claim 6, wherein said core is formed of a first polyamide material, said sheath is formed of a second polyamide material and the melting temperature of said first polyamide material is at least 30° C. greater than the melting temperature of said second polyamide material.

8. A method, as claimed in claim 7, wherein said first polyamide material is Polyamide 66 and said second polyamide material is Polyamide 6.

9. A method, as claimed in claim 1, wherein said repair device is a surgical suture or a mesh implant.

10. A method, as claimed in claim 9, wherein said repair device is a surgical suture or a mesh implant.

11. A method, as claimed in claim 1, wherein said repair device comprises a thin polymeric, substantially planar sheet having non-absorbable imaging nanoparticles substantially uniformly dispersed therein.

12. A method, as claimed in claim 11, wherein said thin polymeric sheet is a polyamide sheet.

13. A method, as claimed in claim 12, wherein said thin polymeric sheet is Polyamide 6 and said repair device is a foil implant.

14. A method, as claimed in claim 1, wherein said imaging material is a particulate material which is detectable by an imaging device selected from x-rays, electromagnetic radiation in the radio frequency domain which is useful for medical imaging, MRI and ultrasound.

15. A method, as claimed in claim 14, wherein said imaging material is non-absorbable, radiopaque nanoparticles substantially uniformly dispersed in said repair device.

16. A method, as claimed in claim 10 wherein said imaging material is non-absorbable, radiopaque nanoparticles substantially uniformly dispersed in said sheath of said suture and in the mesh of said implant.

* * * * *